(12) United States Patent
Summer et al.

(10) Patent No.: US 6,425,760 B1
(45) Date of Patent: *Jul. 30, 2002

(54) TOOTH SPACER

(75) Inventors: John D. Summer, 9601 NW. Leahy Rd., #305, Portland, OR (US) 97229; Gregory B. Stock, Los Angeles, CA (US)

(73) Assignee: John D. Summer, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/611,187

(22) Filed: Jul. 6, 2000

Related U.S. Application Data

(63) Continuation-in-part of application No. 09/465,413, filed on Dec. 16, 1999.

(51) Int. Cl.[7] .............................................. A61C 5/04
(52) U.S. Cl. ........................................................ 433/39
(58) Field of Search ........................... 433/39, 136, 148, 433/155; 264/16

(56) References Cited

U.S. PATENT DOCUMENTS

| | | | |
|---|---|---|---|
| 638,973 A | 12/1899 | Mehlig ........................ 433/40 |
| 804,099 A | 11/1905 | Chase ......................... 433/39 |
| 1,133,379 A | 3/1915 | Hollingsworth .............. 433/39 |
| 1,265,581 A | * 5/1918 | Zurbrigg ..................... 433/39 |
| 1,794,213 A | 2/1931 | Spahn ......................... 433/23 |
| 2,288,011 A | 6/1942 | Mizzy ........................ 433/148 |
| 2,607,117 A | 8/1952 | Baughan ..................... 433/39 |
| 2,790,238 A | * 4/1957 | Trangmar .................... 433/39 |
| 2,835,628 A | 5/1958 | Saffir .......................... 433/39 |
| 3,074,169 A | 1/1963 | Freeman ...................... 433/39 |
| 3,082,531 A | 3/1963 | Jacobsen ..................... 433/39 |
| 3,145,472 A | 8/1964 | Tofflemire ................... 433/39 |
| 3,305,928 A | 2/1967 | Tofflemire ................... 433/39 |
| 3,421,222 A | 1/1969 | Newman ..................... 433/39 |
| 3,842,505 A | 10/1974 | Eames ......................... 433/39 |
| 4,024,643 A | 5/1977 | Eisenberg .................... 433/39 |
| 4,373,915 A | 2/1983 | Comstock .................. 433/136 |
| 4,523,909 A | 6/1985 | Lazarus ....................... 433/39 |
| 4,563,152 A | 1/1986 | McClure ..................... 433/39 |
| 4,608,021 A | 8/1986 | Barrett ....................... 433/229 |
| 4,718,849 A | 1/1988 | von Wissenfluh et al. ..... 433/39 |
| 4,909,736 A | * 3/1990 | Ritter ......................... 433/39 |
| 5,330,353 A | 7/1994 | Wavrin ....................... 433/39 |
| 5,342,194 A | 8/1994 | Feldman ..................... 433/39 |
| 5,380,198 A | 1/1995 | Suhonen ..................... 433/39 |
| 5,505,618 A | 4/1996 | Summer ..................... 433/148 |
| 5,586,883 A | * 12/1996 | Nakisher et al. ............. 433/39 |
| 5,899,694 A | 5/1999 | Summer .................... 433/136 |
| 5,951,801 A | * 9/1999 | Weissenfluh et al. ......... 433/39 |
| 6,142,778 A | * 11/2000 | Summer ...................... 433/39 |

FOREIGN PATENT DOCUMENTS

| | | |
|---|---|---|
| EP | 0241107 A1 | 10/1987 |
| WO | WO 01/43656 A1 | 6/2001 |

OTHER PUBLICATIONS

*Sullivan–Schein Dental Catalogue*, pp. 313–314 (no publication date on these sheets).
*Dental Products*, "Matrix Bands" product description, Jul. 1998.
*Dental Products Report*, Light–Curing Matrix, Nov. 1999.

* cited by examiner

*Primary Examiner*—John J. Wilson
(74) *Attorney, Agent, or Firm*—Klarquist Sparkman LLP

(57) ABSTRACT

A tooth spacer has first and second tooth spacer body portions which each define at least one window therein. Extremely thin film, for example from about 0.0003 to about 0.0006 inch in thickness, is sandwiched between the tooth spacer body portions to form the tooth spacer. Portions of the gingival edge of the tooth spacer may be thinned to facilitate insertion of the tooth spacer between teeth.

40 Claims, 6 Drawing Sheets

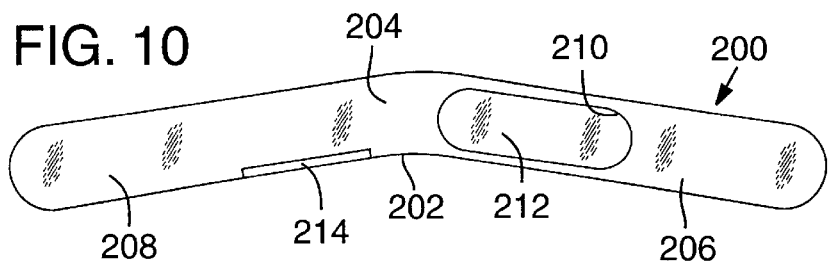
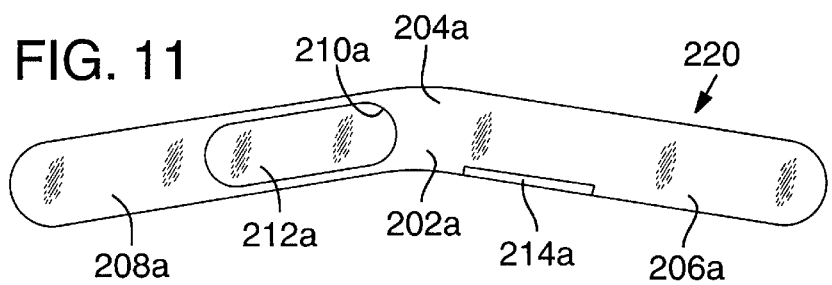
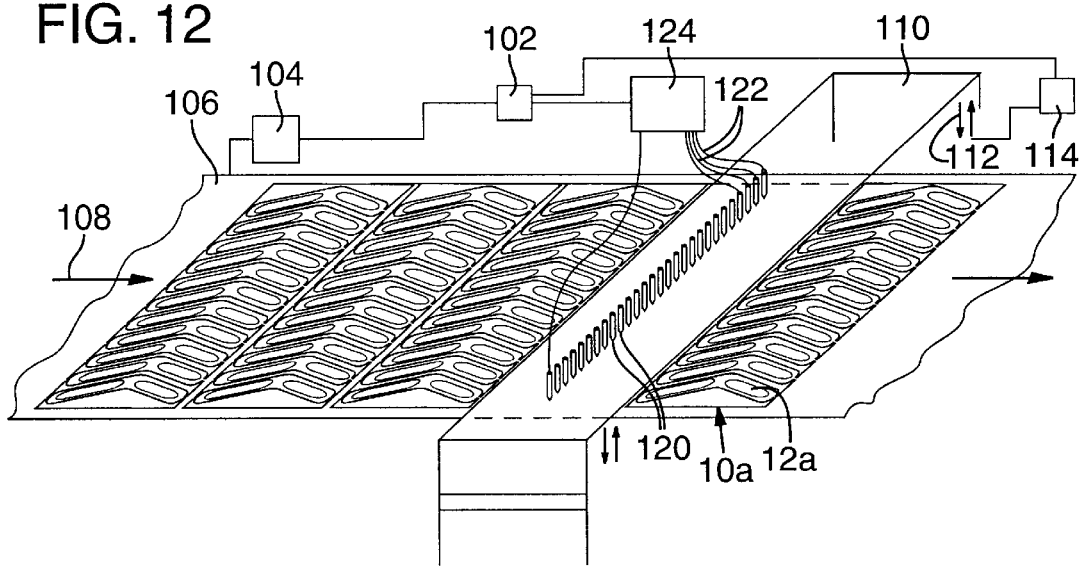

TOOTH SPACER

CROSS REFERENCE TO RELATED APPLICATION

The present application is a continuation-in-part of application Ser. No. 09/465,413 entitled, "Method and Apparatus for Shaping Dental Filling Material" by John D. Summer and Gregory B. Stock, filed Dec. 16, 1999.

BACKGROUND

The present invention relates to tooth spacers and to a method of making a tooth spacer for use in shaping tooth filling material, such as composite resin, which has been placed in a tooth cavity preparation and for other dental applications.

In dentistry, teeth which are subject to decay are typically drilled or otherwise prepared by removing the decayed tooth material and creating a form for receiving filling material. This leaves an aperture, slot or other void in the tooth which needs to be filled with composite resin or other filling material. When dentists fill class 2 cavity preparations, they typically insert a temporary substrate adjacent to the cavity preparation to contain and control the flow of filling material. The temporary substrate that dentists have traditionally used is an elongated band called a matrix band. The bands are typically placed in some type of a retaining device and then tightened around the prepared tooth by rotating a portion of the retaining device with the tightening being accomplished shortly before the filling process is begun. One example of a matrix band is found in U.S. Pat. No. 5,380,198 to Suhonen. This particular band has at least one window covered by a transparent strip of plastic such as cellulose acetate. The plastic strip rests against the dental filling material which may be cured using light. This patent also mentions retaining the matrix band in position with the aid of a matrix tightener such as used in a Tofflemire system.

Since most of the composite resins used to fill teeth today are light cured resins, clear plastic bands offer significant advantages over metal matrix bands. Composite resin can be observed by a dentist through the clear plastic band to ensure that there are no unfilled voids before curing. In addition, the composite resin may then be cured by shining light through the clear plastic band to ensure a better depth of cure. However, clear plastic matrix bands which are known to the inventor have been composed of strips of mylar (polyester) which is at least 0.0015 inch thick or plastic materials such as mentioned in U.S. Pat. No. 5,380,198. The materials in U.S. Pat. No. 5,380,198 are also understood to be relatively thick. This patent equates in one example, the thickness of the plastic to the thickness of a steel band included in the device of e.g., 0.05 mm thickness.

Therefore, there is a need for an improved method for producing tooth spacers for applications such as shaping tooth filling material and for improved tooth spacers. The present invention does not require the solution of all of the problems of the prior art. Instead, the invention is directed toward new and unobvious features and methods set forth in this disclosure both alone and in combination with one another and as set forth in the claims below.

SUMMARY

In accordance with one embodiment, a method of making at least one tooth spacer is disclosed, the tooth spacer being designed for insertion between the interproximal surfaces of at least one pair of adjacent teeth during a dental procedure, the adjacent teeth having a proximate area where the teeth are closest to or in contact with one another. In accordance with the method of this embodiment, first and second tooth spacer body portions are provided which each have at least one opening therethrough. A film is positioned at least partially between the first and second tooth spacer body portions. The respective openings through the tooth spacer body portions are at least partially aligned with one another and the film is visible through at least the aligned portions of the at least partially aligned openings. The film and first and second tooth spacer body portions are interconnected such that only the thickness of the film is present at least at one proximate tooth contact location of the tooth spacer. The at least one proximate tooth contact location is positioned where the openings are at least partially aligned and the film is present. As a result, the at least one proximate tooth contact location of the tooth spacer may be positioned at the proximate area between the adjacent teeth. In this case, only the thickness of the film is present in the proximate area between the adjacent teeth. The tooth spacer with the film is usable in shaping filling material especially in the proximal part of the tooth being filled.

The film may be a thin polymer sheet material. Preferably, the thickness of the sheet material film positioned between the proximal or adjacent most surfaces of the two adjacent teeth during filling of one of the teeth is no more than 0.0005 inch and desirably from about 0.0003 inch to 0.0006 inch. A light transmissive material or optically transparent material such as clear polyethylene may be used. The two body portions hold the film in place to span at least the aligned portions of the at least partially aligned openings. The assembled tooth spacer is flexible enough in one form so that it can be easily bent or wrapped at least partially around a tooth to be filled. The tooth spacer body portions may be elongated so that they may be wrapped entirely around a tooth with the tooth spacer being flexible enough to closely follow the natural unprepared contours of the tooth being filled. In some applications a conventional mechanism may be used to tighten the tooth spacer and to hold it in place during the dental procedure.

The tooth spacer body portions may be of the same or of a different thickness and may also have a total thickness which is no greater than 0.003 inch to 0.004 inch without the thickness of the film. As a specific example, if the tooth spacer body portions are of the same thickness, they may each, for example, have a thickness which is no greater than 0.002 inch, with 0.0015 inch being a more specific example. Each of the tooth spacer body portions may be formed from sheet material which may be of a homogenous single layer of material such as metal, with stainless steel being a specific example. The film may also be a single layer of film. Alternatively, and less desirably, the components of the tooth spacer body portions may be laminated of multiple layers.

In a more specifically desirable embodiment, the tooth spacer body portions may be of an identical size and shape and may be substantially aligned with one another with the openings through the respective body portions also being substantially aligned. By substantial alignment it is meant that the boundaries of the openings match one another within manufacturing tolerances as opposed to being deliberately offset.

In accordance with another aspect, each tooth spacer body portion may be elongated with at least first and second spaced apart openings. The first opening in the first tooth spacer body portion may be at least partially aligned with the first opening of the second tooth spacer body portion. In addition, the second opening of the first tooth spacer body portion may be at least partially aligned with the second opening of the second tooth spacer body portion. In addition, the film may entirely span the first and the second at least partially aligned openings. In this example, when the tooth spacer is wrapped around a tooth, the respective first openings may be positioned in the proximate area between the tooth and a first adjacent tooth and the respective second openings may be positioned in the proximate area between the tooth and a second adjacent tooth with the second adjacent tooth, being on the opposite side of the tooth from the first adjacent tooth.

Interconnection of the first and second tooth spacer body portions with the film may be accomplished in a number of ways such as adhesively or otherwise. Desirably this interconnection is accomplished at least in part by compressing and heating the film to heat fuse or heat seal the film and first and second tooth spacer body portions together. The film may be heated and simultaneously compressed at plural discrete spaced apart locations. Elongated heating elements may be utilized to apply both heat and pressure to one or both of the tooth spacer body portions to accomplish this heat fusion. The portion of the film exposed at the openings may be shielded from heat to prevent distortion of the film.

As a further aspect, the tooth spacer has a gingival edge portion which is to be positioned next to the gingiva of a patient during a dental procedure. At least one of the first and second tooth spacer body portions, and in one approach each of the first and second tooth spacer body portions, have a gingival edge portion with a section of reduced thickness to facilitate insertion of the interconnected tooth spacer between the adjacent teeth.

As another aspect, the openings through which the film is exposed when the tooth spacer is assembled may be spaced inwardly from the perimeter edge of the tooth spacer body portions and of the assembled tooth spacer such that the film in the openings is entirely surrounded by a portion of the respective tooth spacer body portions.

First and second elongated tooth spacer body portions may be provided which, when interconnected into a tooth spacer, have first and second side portions disposed on opposite sides of a central portion. In one form, only one of the respective first and second side portions may have at least partially aligned openings in the first and second elongated tooth spacer body portions through which the film is visible. The tooth spacer has a gingival edge and this embodiment may include reducing the thickness of a portion of the gingival edge along the one of the first and second side portions which does not have the at least partially aligned openings.

In a specific approach, the tooth spacer may be formed from a stack comprised of a first sheet which defines a plurality of first tooth spacer body portions and a second sheet which defines a plurality of second tooth spacer body portions. The stack also includes a sheet of film positioned between these first and second sheets. In this example, first tooth spacer body portions on the first sheet are aligned with second tooth spacer body portions on the second sheet. In addition, the first tooth spacer body portions and second tooth spacer body portions each include at least one opening with respective openings of first tooth spacer body portions being at least partially aligned with corresponding respective openings of the second tooth spacer body portions and with the film spanning and being visible through the at least partially aligned openings. The sheets and film are then interconnected, such as by heat fusing. The individually defined tooth spacer body portions may be connected to their respective sheets by severance portions which are then severed following the interconnection of the sheets and film to form the individual tooth spacers. Again, the tooth spacers may include two or more spaced apart openings. In addition, the respective sheets may be each provided with at least one alignment opening and more typically with at least two such alignment openings to facilitate the alignment of the sheets and film which are to be assembled into the tooth spacers.

In the event heat fusion is used to assemble the tooth spacers, typically heat is applied at locations spaced from the openings so as to not adversely affect film exposed in the openings. In addition, the film may be heat fused at discrete locations spaced about the entire periphery of the aligned openings.

Additional features of embodiments of the present invention are set forth in the detailed description below and shown in the drawings. The invention includes novel and unobvious elements, acts, features and methods described here both individually and collectively and is not limited to any specific exemplary embodiments or approaches.

BRIEF DESCRIPTION OF THE DRAWINGS

FIG. 10 illustrates an embodiment of a tooth spacer having at least partially aligned openings through which film is visible which are positioned along one side portion of the tooth spacer and in which the gingival edge portion of the opposite side portion of the tooth spacer has a section of reduced thickness.

FIG. 11 illustrates a form of tooth spacer similar to FIG. 10 but with the gingival edge portion of a reduced thickness positioned on the opposite side portion of the tooth spacer from that shown in FIG. 10.

FIG. 12 schematically illustrates an alternative method for applying heat to tooth spacers utilizing a line of plural heating elements which are applied to a stack of a first tooth spacer body portion, a film, and a second tooth spacer body portion as the stack is passed incrementally beneath it in order to heat fuse the stack into tooth spacers which are then individualized.

DETAILED DESCRIPTION

With reference to the figures, several tooth spacer embodiments methods of making tooth spacers will be described.

Figure 1:
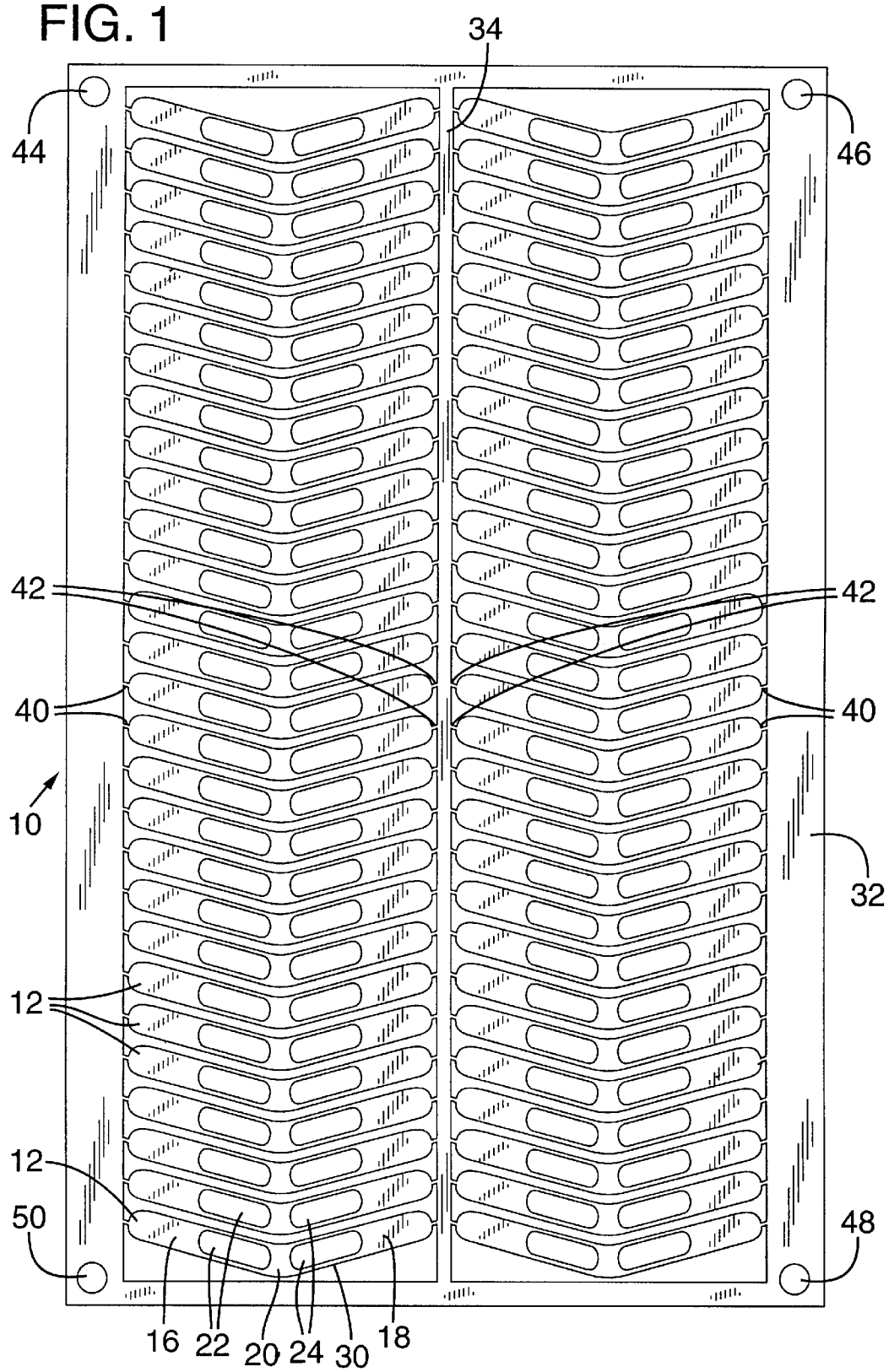
FIG. 1 is a top plan view of a sheet having a plurality of first tooth spacer body portions of one specific form defined thereon, each of the first tooth spacer body portions being connected to the sheet by at least one severance element or portion, it being understood that sheets of second tooth spacer body portions may be identical to the sheet of FIG. 1.

FIG. 1 illustrates a sheet of material 10 having a plurality of exemplary tooth spacer body portions defined thereon with some tooth spacer body portions denominated by the number 12. The tooth spacer body portions may assume different shapes and configurations other than shown in this figure. In the form shown, the tooth spacer body portions are elongated and angular or wing-like in shape. Each tooth spacer body portion includes a first side portion 16, a second side portion 18 and a central portion 20. Each of the tooth spacer body portions may include at least one opening therethrough. In the form shown in FIG. 1, each of the tooth spacer body portions 12 have two such spaced apart openings, indicated generally at 22 and 24 on several of the tooth spacer body portions shown in FIG. 1. The openings 22, 24 may be elongated with rounded edges or they may be otherwise shaped. In the illustrated form, the openings 22, 24 are spaced inwardly from the perimeter edge 30 of the tooth spacer body portion such that the respective openings are each surrounded on all sides by a portion of the tooth spacer body portion 12.

The illustrated sheet 10 includes a peripheral side margin 32 which extends around the entire sheet in the form shown. One or more internal strip portions as for example 34 extends between the upper and lower edges of the sheet in FIG. 1. Each of the illustrated tooth spacer body portions 12 is connected by at least one severance portion to the remainder of the sheet. In the form shown in FIG. 1, two such severance portions 40, 42 are provided for each tooth spacer body portion 12. In this example, severance portions 40 connect the ends of tooth spacer body portions to the perimeter sheet portion 32 and severance portions 42 connect the opposite ends of the tooth spacer body portions to the retention strip 34.

The sheet 10 may include at least one alignment opening, and in the embodiment shown, includes four such alignment openings 44, 46, 48, and 50 at the respective corners of the sheet 10. The purpose of the alignment openings will be apparent from the discussion below.

The sheet 10 may comprise a laminated sheet or may be a single homogenous layer of material with stainless steel being a specific example. The sheet typically is relatively thin, such as being of a uniform thickness of from about 0.001 inch to about 0.002 inch in thickness. A specific example is a 0.0015 inch thick sheet of stainless steel. Although possible for the sheet to be of non-uniform thickness with, for example, thin portions of the sheet located to be positioned in the proximate area between teeth, this would be expected to increase manufacturing costs. Conventional chemical etching or photo etching techniques may be used to form the tooth spacer body portions 12 with the respective openings 22,24 and severance portions 40, 42.

Figure 2:
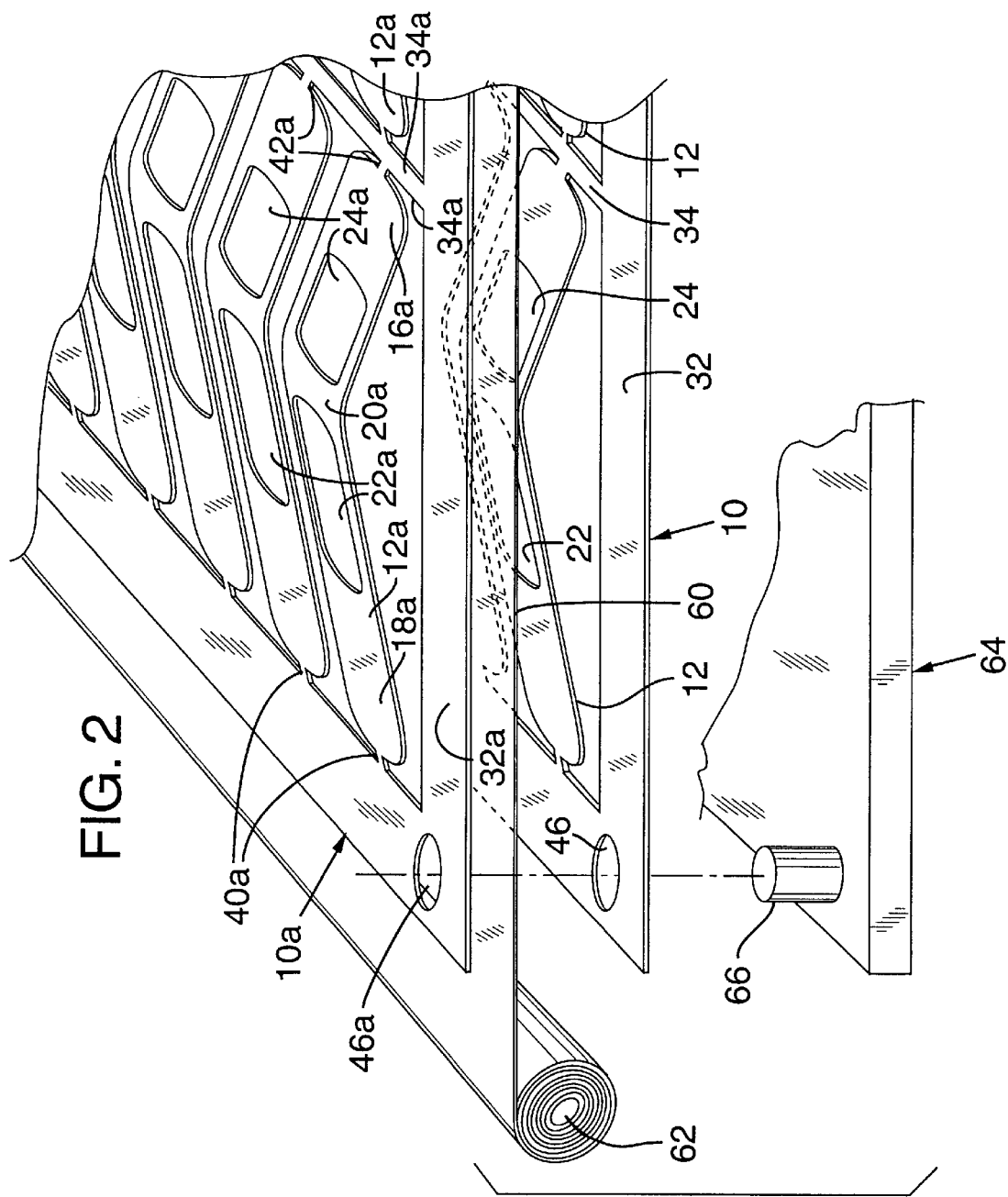
FIG. 2 illustrates a stack consisting of a first sheet containing a defined plurality of first tooth spacer body portions, a sheet of polymer film shown with an exaggerated thickness, and a second sheet containing a defined plurality of second tooth spacer body portions, it being understood that the tooth spacer body portions may have configurations other than those shown in FIG. 2.

A second sheet, which may be identical to the sheet of FIG. 1, may be combined with the sheet of FIG. 1 and other elements into a tooth spacer assembly with the individual tooth spacers then being separated following the interconnection of the assembly. For example, FIG. 2 illustrates a tooth spacer body portion defining sheet 10a. The elements of sheet 10a which correspond to the elements of sheet 10 have been assigned the same numbers with the added designation "a" for convenience and for this reason will not be discussed further. The sheet 10a may be of the same material as the sheet 10. It is not necessary that the sheets are of the same thickness or that the tooth spacer body portions 12, 12a are of the same size or shape. In addition, the openings 22, 22a and 24, 24a may be partially aligned or substantially entirely aligned in a more desirable embodiment.

The assembly shown in FIG. 2 includes at least one sheet of film material 60 which is positioned so as to span the aligned portions of the sets of openings 22, 22a and 24, 24a of the respective tooth spacer body portions. Most preferably, the sheet spans the entirety of the openings through each of the respective tooth spacer body portions which are included in the respective tooth spacers. The stack of sheets 10 and 10a may be positioned on an alignment jig 64 with sheet 60 stretched taut between them. A pin 66 of the alignment jig may be inserted through the openings. 46 and 46a at each of the corners of the assembly.

The sheet 60 may be a film of a light transmissive material so as to permit the passage of light through the film to cure conventional light curable tooth filling materials which are commonly used in dentistry today. By light transmissive it is meant that the material, when illuminated, allows passage of sufficient light to cure the filling material. Most preferably the material is of a clear plastic such as of a polyethylene film having a thickness of from about 0.0003 inch to about 0.0006 inch. When the individual tooth spacers are assembled, the tooth spacer body portions which support the film add sufficient strength to minimize the possibility of tearing of the film. Even though extremely thin, the film is still useful in shaping filling material along the sides of a tooth being filled.

In the embodiment of FIG. 2, one sheet of polymer material is used. Although less desirable, multiple sheets may be included or a laminated sheet may be used. In FIG. 2, an elongated sheet 60 which has been rolled up on a shaft 62 or other dispenser has been unrolled so as to entirely span the tooth spacer body portions, but not necessarily the peripheral side margins of the two sheets 10, 10a. Sheet 60 may be stretched or tensioned in this position from two or more sides so that it is held taut between sheets 10 and 10a while at least a portion of the heat sealing occurs. A tensioning clamp which grips the film or manually applied tension are examples of suitable approaches for applying tension. The shaft 62 may have a brake, stop or friction applying mechanism to prevent or resist unrolling of the film. Conventional boxes of film, such as Handiwrap® film, dispense film through a tension-applying slit and is one specific approach that may be used.

As can be seen in FIG. 2, when stacked in this manner the sheet 60 is sandwiched between the sheets 10 and 10a. The sheet 60 may be heat-sealed or otherwise affixed to the sheets 10, 10a to thereby assemble the stack of sheets into respective tooth spacer assemblies.

In one specific approach, the peripheral margins of sheets 10, 10a may be heated to adhere the film and sheets together at such locations and thereby maintain the film taut during subsequent assembly steps. The film may then be separated from the roll 62 and the stack subsequently heat processed to assemble each of the tooth spacer assemblies. Alternatively, heat sealing may be completed while the stack is on holder 64.

The large centrally located openings 22, 22a and 24, 24a with the film therein may be positioned in the proximate area between a tooth to be treated and an adjacent tooth or teeth as explained more fully below.

Figure 3:
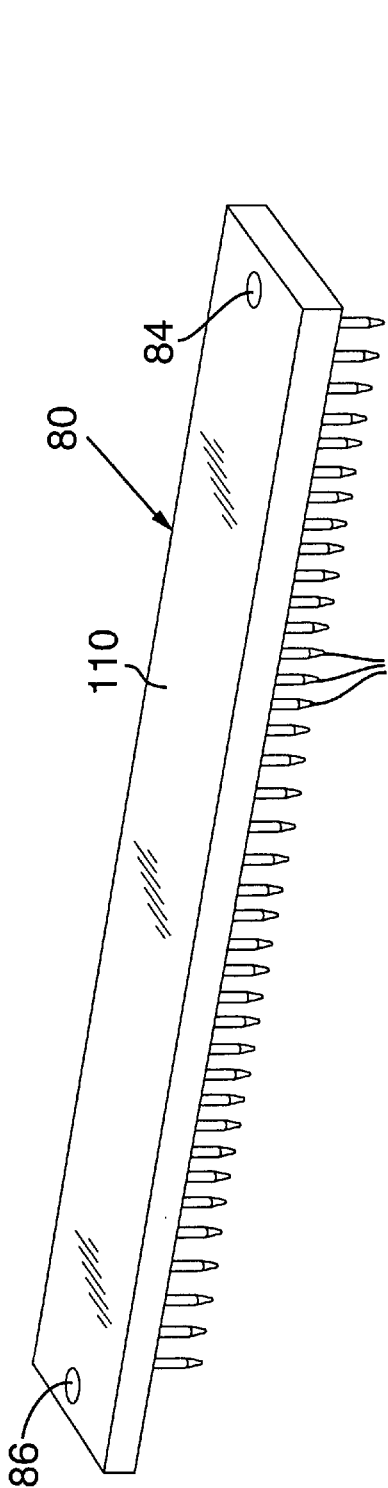
FIG. 3 is a partially broken away perspective view of a portion of one form of heating element which may used in heat fusing the sheets and film of FIG. 2 together.
Figure 4:
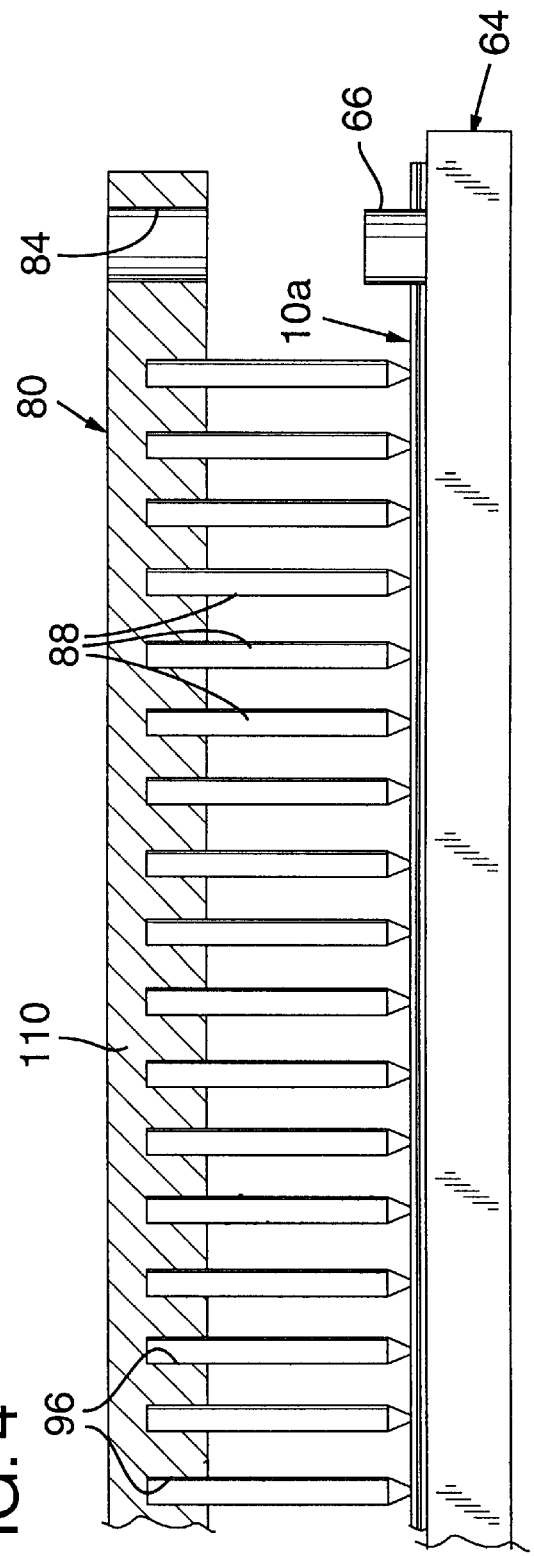
FIG. 4 is a vertical sectional view showing a stack of two such heating elements with a stack comprised of first and second tooth spacer body portion containing sheets and the film positioned between the heating elements.

A number of approaches may be utilized to heat seal the tooth spacer forming components together. Heat fusing may, for example, be substantially continuous in areas spaced from the portion of the film exposed through the openings. Alternatively, the components may in effect be spot-welded together at a plurality of discrete spaced apart locations. Heat may be applied in any suitable way to accomplish the desired heat fusion. In addition, the exposed film in the openings may be shielded by a heat shield if desired with moist tissue being one specific example of such a shield. FIGS. 3, 4, and 12 illustrate one specific approach for accomplishing heat sealing. In FIGS. 3, 4 and 12, a plurality of elongated heating elements such as heat transfer pins, some being indicated at 88, are mounted in heating element support 110. The elongated pins 88 have tapered ends and are typically of a heat transmissive material, such as metal, which may be heated, such as electrically, like individual soldering iron tips. The pins 88 are arranged in a desired pattern to apply heat and pressure to the respective tooth spacer body portions located on the sheets 10, 10a without applying sufficient heat at locations where it would damage film exposed through the openings 22, 22a and 24, 24a in the tooth spacer body portions 12, 12a. The pins 88 as well as heating element support 110 and support base 64 are typically designed to be able to deliver and withstand considerable compressive forces between support 110 and the stack supporting base 64. For example, a pressure (which may be varied) in the range of about two pounds to ten pounds, may be applied by each pin 88 during heat sealing.

Figure 5:
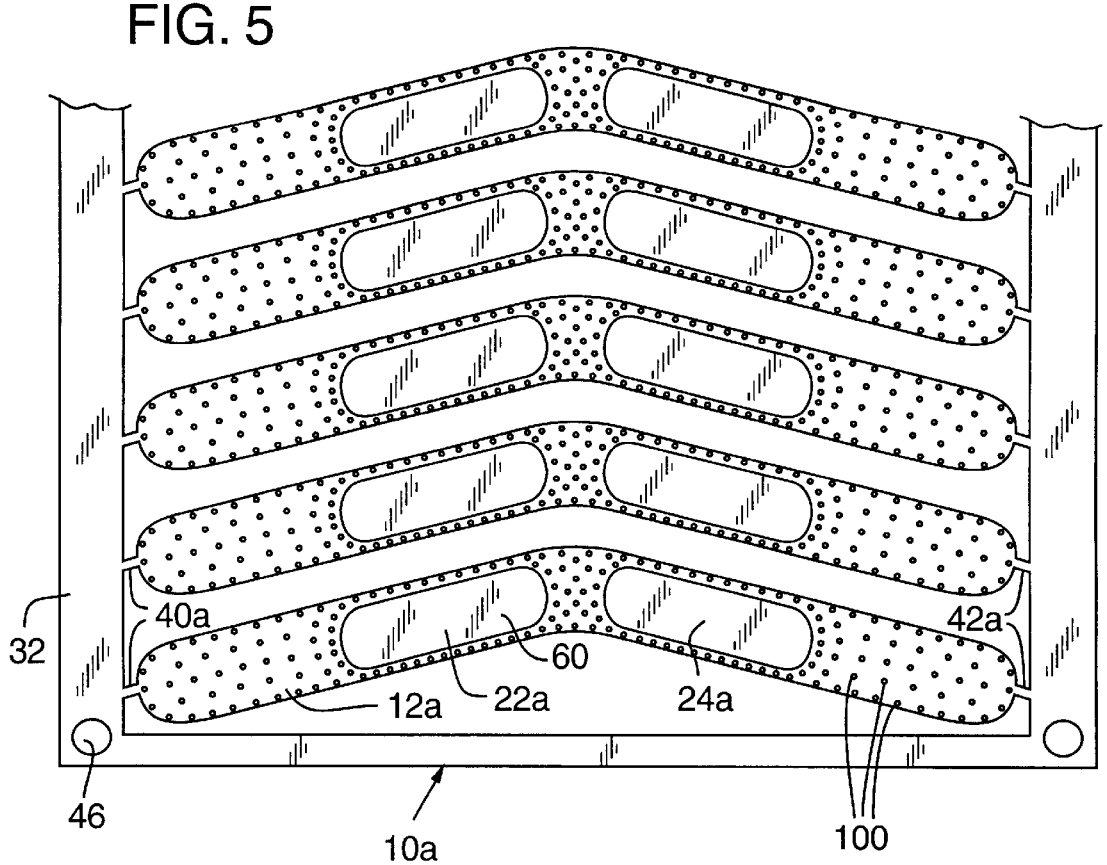
FIG. 5 is a top plan view of assembled tooth spacers showing an exemplary pattern of discrete spaced apart heat fusing locations where the components have been subjected to heat and pressure by the heating elements of FIGS. 3 and 4.
Figure 5A:
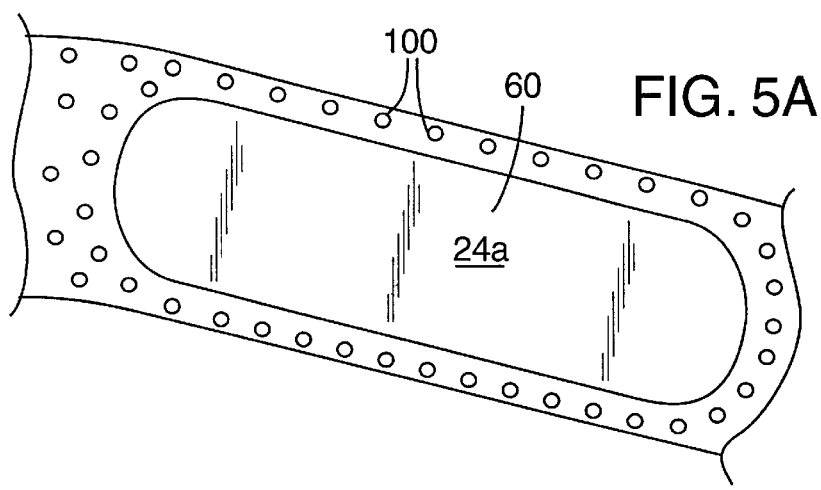
FIG. 5A is an enlarged view of a portion of one of the tooth spacer assemblies of FIG. 5 schematically illustrating a pattern of heat fused locations positioned about the entire periphery of substantially aligned openings in the first and second tooth spacer body portions through which the film is visible.

FIG. 5 illustrates one exemplary pattern of spot welds with some being numbered as 100. The spot welds are shown located at discrete spaced apart locations, although this is not necessary. FIG. 5a illustrates an exemplary pattern of spot welds 100 showing the spot welds positioned around the entire periphery of the film containing window opening 24a.

FIG. 12 illustrates bonding the tooth spacer components together. In FIG. 12, a controller 102 is shown which may be a conventional computer with a keyboard or other input device, a screen and associated memory. A driver or motor, such as a stepper motor 104, is drivenly coupled to a conveyor, such as a belt 106, and controlled by controller 102 and associated driver circuitry for moving the conveyor in a direction indicated by arrow 108 in stepped increments. A heating element support 110 is movable upwardly and downwardly relative to the conveyor as indicated by arrows 112. A mechanism, such as an electric or a pneumatic actuator, shown schematically in FIG. 114, is controlled by controller 102 and associated control circuitry to raise and lower the heating element support 110. The support is raised when conveyor 106 is advanced and lowered when desired to apply heat to the respective tooth spacer assemblies. A plurality of elongated heating elements 120, which may be like pins 88, are supported by support 110 and project downwardly from the support. Elements 120 may be arranged in a suitable pattern or array, such as in a linear array as illustrated in FIG. 12. Elements 120 may comprise soldering iron tips which are selectively heated in response to electrical current being passed along conductors 122 to the respective tips 120 under the control of a current switching circuit 124. In response to signals from computer 102, appropriate switches in circuit 124 are operated to allow current to flow to the desired soldering iron tips to which heat is to be supplied for the desired heat fusion pattern on the portions of the tooth spacer assemblies which are underneath the array of soldering iron tips. Following completion of each line of heat welds, the tips are raised and the conveyor is advanced. The tips are again lowered with the appropriate tips then being heated. The mechanism of FIG. 12 thus provides heat and pressure to the tooth spacer components and may provide a heat fusion pattern on these elements such as shown in FIG. 5. For purposes of convenience, FIG. 12 does not show alignment jigs or other alignment devices which would maintain the tooth spacer components in alignment as the soldering takes place.

Typically, following heat fusing or other interconnection, the individual tooth spacers are separated from the sheets 10, 10a by breaking the severance portions 40, 40a, 42, 42a. In one photo etching approach for producing the sheets, a mask is applied over those portions of the sheets which are not to be etched. By applying a mask to each side of a sheet such as sheet 10a and etching from both sides, the openings 22a, 24a are formed. In addition, portions of the sheet between the respective tooth spacer body portions 12a are also removed except for the severance elements 40a, 42a. The mask has voids at locations of the openings and where material between the tooth spacer body portions is to be removed. In addition, the severance elements may be rendered thinner than the tooth spacer body portions and remaining portions of the sheet (e.g., 32a, 34a) to which the tooth spacer body portions are coupled by the severance portions. As one specific approach, the portion mask may be eliminated on one side of the sheet where the severance elements are to be located such that etching is allowed to take place from that one side. The severance element remains intact in this case because etching of the severance elements does not take place from the other side where they are masked and it is the combination of etching from both sides of the sheet in this example that totally removes material to provide the desired openings and separation between the tooth spacer body portions.

The interconnected tooth spacers may then be individualized by severing the severance portions. Alternatively, tooth spacers may be made one at a time. In this case, heat fusion may be accomplished using, for example, a soldering iron.

Figure 6:
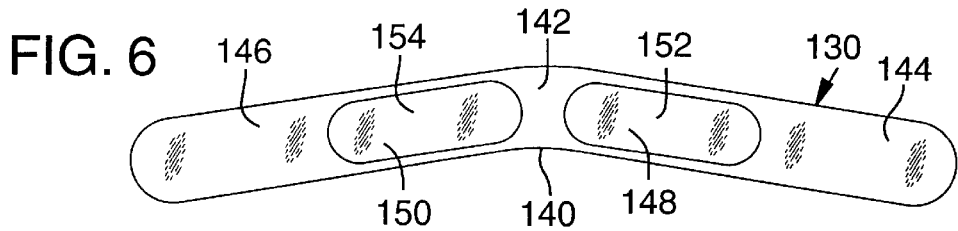
FIG. 6 is a side view of one form of individual assembled tooth spacer having two spaced apart openings spanned by the film.

An individual tooth spacer 130 is shown in FIG. 6. As can be seen in this figure, the completed tooth spacer in this form has a gingival edge 140, a central portion 142, a first side portion 144, and a second side portion 146. In this embodiment, the side portions 144, 146 each have a respective opening 148, 150 spanned by polymer material 152, 154 (e.g., portions of the sheet 60). The tooth spacer has the polymer material sandwiched between first and second tooth spacer body portions, in this case the tooth spacer body portions having substantially aligned openings to define the respective windows 148, 150.

Figure 7:
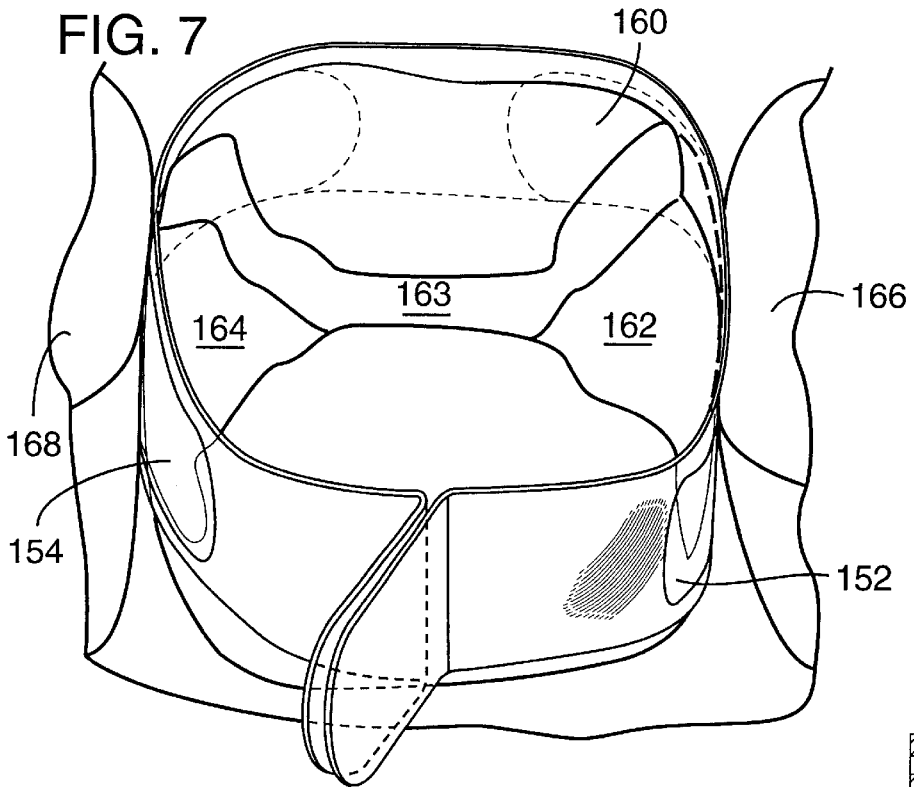
FIG. 7 is a perspective view of a tooth spacer of the form shown in FIG. 6 positioned with one of the film containing sets of openings located in the proximate area between a tooth to be treated and an adjoining tooth and the film containing sets of other openings located in the proximate area between the tooth and an adjoining second tooth.

FIG. 7 illustrates a tooth 160 which has been prepared to receive a filling, in this case producing a channel in the tooth 160 having a section 162 next to a first adjacent tooth 166, a central portion 163, and a third portion 164 at the side of tooth 160 adjacent to another tooth 168 which is opposite to the tooth 166. As can be seen in FIG. 7, only the polymer film 152, 154 is present at the proximate area of the adjacent teeth 160, 166 and 160, 168 where they are closest to one another. Consequently, as filling material is deposited and packed into the channel, the film 152, 154 assists in shaping the filling and provides desirable spacing between the filling material when cured and the adjacent teeth.

One specifically suitable film for windows 152, 154 (and sheet 60) is a polyethylene film sold under the brand name HandiWrap® by S.C. Johnson & Son, Inc., of Racine, Wis. This film is about 0.0005 inch thick. While other plastics such as polyester, polyurethane, or polyolefin may be used, polyethylene is preferable for several reasons.

Preferably, a material such as polyethylene which has a dead-soft quality is selected. Such a material is extremely pliable without memory. The newer composite resins used in fillings are especially designed to have the same dead-soft quality so that they can be shaped with a stroke of an instrument and then will not slump or undergo any other changes in form unless further manipulated. When these new composite filling materials are used together with a polyethylene or other dead-soft film, it becomes easy to shape the final contours as needed using a simple hand instrument before curing. Curing may then be accomplished, for example, with light. By using a light transmissive film, the filling material may be cured through the tooth spacer windows 152, 154 as well as from above.

It is also desirable to select a material like polyethylene which is slightly stretchable. When placed under pressure, such a film stretches in a way that tends to cause the central section of the film, in this case the portion of the film spaced from the surrounding tooth spacer body portions, to extend or pouch-out and form a gradual curve that gives the film material a contour much like the side of a natural tooth. Such contours which reproduce natural tooth contours are highly desirable.

A conventional matrix tightening mechanism such as a Tofflemire mechanism may be used to tighten the tooth spacer of the embodiment of FIG. 7. Other tightening mechanisms may also be used.

Figure 8:
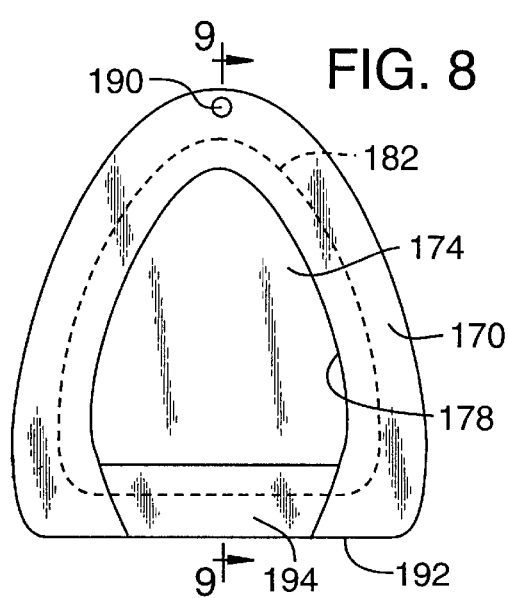
FIG. 8 illustrates an alternative form of tooth spacer in which at least one of the tooth spacer body portions has a reduced thickness beneath the openings which are spanned by the film.
Figure 9:
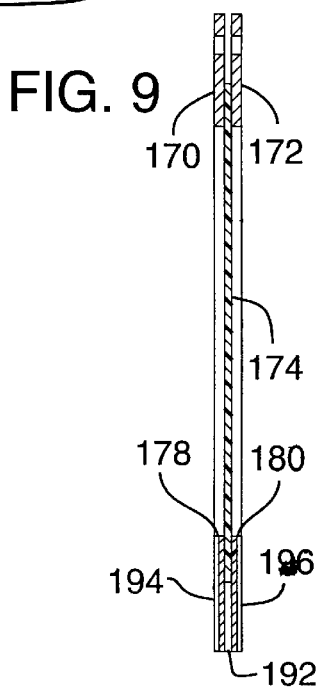
FIG. 9 is a vertical sectional view taken generally along the direction along line 9—9 of FIG. 8 showing an embodiment with the gingival edge portion of each of the two spacer body portions having a section of reduced thickness, the film shown in FIG. 9 having an exaggerated thickness.

FIGS. 8 and 9 illustrate a form of tooth spacer having respective tooth spacer body portions 170, 172 which are of a generally triangular shape. The tooth spacer illustrated in FIGS. 8 and 9 is anatomically shaped to fit between front teeth. A tooth spacer designed for the rear teeth would be more rectangular shaped. These embodiments illustrate the fact that the tooth spacer body portions may assume configurations other than shown in FIG. 1. In addition, a polymer film 174 is shown sandwiched between the tooth spacer body portions 170, 172. The tooth spacer body portions and film may be interconnected in the same manner as previously described in other embodiments. For example, the elements may be heat fused together. In the form shown in FIG. 8, film 174 spans an entire window defined by openings 178, 180 provided in the respective tooth spacer body portions 170, 172. The openings may be at least partially aligned or substantially entirely aligned as shown in FIGS. 8 and 9. The film 174 may have an edge 182 which is spaced inwardly from the outer edge of the tooth spacer body portions. Alternatively, the film 182 may be co-extensive with the body portions of the finished tooth spacer. The film and first and second tooth spacer body portions of FIGS. 8 and 9 are desirably formed of the same materials and thicknesses as previously described. In these FIGURES the film is shown with an exaggerated thickness for convenience only. Each of the respective body portions may include an opening 190 at an upper region thereof. The openings 190 facilitate use of the tooth spacer. For example, a dental tool, such as a pick, may be inserted into the openings 190 and used to lift upwardly and remove the spacer following completion of the dental treatment.

The spacer of FIGS. 8 and 9 includes a gingival edge portion 192. One or both of the tooth spacer body portions 170, 172 may have at least one section along the gingival edge which is of a reduced thickness to facilitate insertion of the tooth spacer between the interproximal surfaces of adjacent teeth. This thin region is indicated at 194 in FIG. 8. Again, each of the tooth spacer body portions may be thinned. Consequently, in FIG. 9 a second thinned region is also shown at 196. These thinned regions may be formed by differential etching in the same manner as the severance portions of the sheet of FIG. 1 are formed, or by use of any other suitable technique such as abrasion.

FIG. 10 illustrates an alternative form of tooth spacer 200. The tooth spacer 200 is elongated with a gingival edge 202, a central portion 204, and first and second side portions 206, 208. In this example, the first and second tooth spacer body portions define the boundaries of a window 210 through which film 212 is exposed. However, the second side portion 208 has no such window. These tooth spacer body portions and film desirably have the same thicknesses as described previously in connection with FIGS. 1–6. The second side portion 208 may include at least a section of reduced thickness along the gingival edge, in this case indicated at 214. This thickness may be, for example, about one-half millimeter wide. The thinned edge section may be formed in a suitable manner, such as by photo etching. The edge sections may, for example, be thinned to a thickness of about 0.0005 inch. This thickness may vary. The form of tooth spacer shown in FIG. 10 is particularly suitable for the mesial surfaces of upper or the distal surfaces of lower teeth. In addition, this single windowed band is typically used when a tooth has a cavity on only one side, which is true of about 75 percent of cavities. In this application, the window is positioned in the proximate area where tooth material has been removed in preparation for a filling. The side portion without the window, side portion 208, is positioned between the interproximal surfaces of the tooth and adjacent tooth where no cavity preparation has been made. The combination of a thinned gingival edge and lack of a window on the side which does not have the cavity preparation, and where the tooth is undrilled or unbroken, makes it easy to slide this portion of the tooth spacer down through the intact interproximal contact area of the non-cavity side of the tooth being filled.

FIG. 11 illustrates a form of tooth spacer 220 which is like the form shown in FIG. 10, but which is most suitable for the distal surfaces of upper or the mesial surfaces of lower teeth. In this case, the window and thinned areas are at the opposite side portions from those shown in FIG. 10. For convenience, elements in the FIG. 11 form of tooth spacer which are in common with elements of the FIG. 10 tooth spacer form have been assigned the same numbers as in FIG. 10 with the added letter "a" and hence will not be described further. The bands of FIGS. 10 and 11 may be held in place in the same manner as the band of FIG. 7.

Having illustrated and described the principles of my invention with reference to a number of embodiments, it should be apparent to those of ordinary skill in the art that the invention may be modified in arrangement and detail without departing from the principles of the invention. For example, the apparatus may be sized to wrap at least partially around more than one tooth, but in this case the apparatus would still be positioned at least partially between the interproximal surfaces of two teeth. I claim all such embodiments and modifications which fall within the scope of the following claims.

We claim:

1. A tooth spacer comprising:
    a first tooth spacer body portion having at least one first opening therein;
    a second tooth spacer body portion having at least one first opening therein;
    the first and second tooth spacer body portions being stacked with the at least one first opening of the first tooth spacer body portion being at least partially aligned with the at least one first opening of the second tooth spacer body portion;
    a film positioned at least partially between the first and second tooth spacer body portions and spanning at least the aligned portions of the respective first openings; and
    the first tooth spacer body portion, second tooth spacer body portion and film being interconnected to form the tooth spacer.

2. A tooth spacer according to claim 1 consisting only of a single first tooth spacer body portion, a single second tooth spacer body portion and the film.

3. A tooth spacer according to claim 1 in which the first tooth spacer body portion, the second tooth spacer body portion and the film are heat fused together.

4. A tooth spacer according to claim 3 in which the first tooth spacer body portion, the second tooth spacer body portion and the film are heat fused together at spaced apart locations.

5. A tooth spacer according to claim 1 in which the film has a thickness which is no greater than 0.0005 inch and the total thickness of the first and second tooth spacer body portions together is no greater than 0.003 inch without the thickness of the film.

6. A tooth spacer according to claim 1 having a gingival edge portion and wherein at least a section of the gingival edge portion of at least one of the first and second tooth spacer body portions is of a reduced thickness.

7. A tooth spacer according to claim 1 wherein each of the first and second tooth spacer body portions is formed from sheet material which is a homogenous single layer of material.

8. A tooth spacer according to claim 1 in which the film is transparent.

9. A tooth spacer according to claim 1 wherein each tooth spacer body portion is elongated and includes at least first and second spaced apart openings, the first opening of the first tooth spacer body portion being at least partially aligned with the first opening of the second tooth spacer body portion and the second opening of the first tooth spacer body portion being at least partially aligned with the second opening of the second tooth spacer body portion, the film entirely spanning the first and second at least partially aligned openings, whereby when the tooth spacer is wrapped around a tooth, the respective first openings may be positioned in the proximate area between the tooth and a first adjacent tooth and the respective second openings may be positioned in the proximate area between the tooth and a second adjacent tooth, the second adjacent tooth being on the opposite side of the tooth from the first adjacent tooth.

10. A tooth spacer according to claim 9 in which the first and second tooth spacer body portions each have a perimeter edge, and wherein each of the first and second openings is spaced inwardly from the perimeter edge so as to be entirely surrounded by a portion of the respective tooth spacer body portion.

11. A tooth spacer according to claim 9 wherein the respective first openings of the respective first and second tooth spacer body portions are substantially entirely aligned and wherein the respective second openings of the first and second tooth spacer body portions are substantially entirely aligned.

12. A tooth spacer according to claim 1 in which the first and second tooth spacer body portions each have at least one opening that is entirely surrounded by a portion of the respective tooth spacer body portion having the opening.

13. A tooth spacer according to claim 1 in which the first and second tooth spacer body portions are elongated and when interconnected into a tooth spacer have first and second side portions disposed on opposite sides of a central portion of the tooth spacer, wherein the at least partially aligned openings through the first and second tooth spacer body portions are provided at only one of the respective first and second side portions, the tooth spacer having a gingival edge, and wherein the thickness of at least a section of the gingival edge is reduced at least along the one of the first and second side portions which does not have the at least partially aligned openings.

14. A tooth spacer according to claim 1 wherein only the first and second tooth spacer body portions and film are interconnected into the tooth spacer such that the maximum number of layers in the tooth spacer is three.

15. A tooth spacer assembly containing a plurality of unseparated tooth spacers which when separated are intended for insertion between the interproximal surfaces of at least one pair of adjacent teeth during a dental procedure, the adjacent teeth having a proximate area where the teeth are closest to or in contact with one another, the tooth spacer assembly comprising:
    a first sheet of body forming material with a plurality of individual first tooth spacer body portions defined thereon, the first tooth spacer body portions being connected to the first sheet by at least one severance portion;
    a second sheet of body forming material with a plurality of individual second tooth spacer body portions defined thereon, the second tooth spacer body portions being connected to the second sheet by at least one severance portion;
    the individual first and second tooth spacer body portions each defining at least one opening;
    a film positioned at least partially between the first and second sheets of body forming material with the first and second sheets of body forming material aligned such that the individual first spacer body portions on the first sheet and the openings therein are respectively at least partially aligned with respective individual second spacer body portions on the second sheet and the openings therein; and
    the film and the first and second body portions of each sheet being interconnected, whereby severing the severance portions separates the individual tooth spacers from the first and second sheets.

16. The tooth spacer assembly of claim 15 in which each of the first and second tooth spacer body portions includes at least two spaced apart openings, the film entirely spanning the at least two openings included in each of the first and second tooth spacer body portions, the at least two openings of each first tooth spacer body portion being substantially aligned with the at least two openings of a respective corresponding second tooth spacer body portion.

17. The tooth spacer assembly of claim 15 wherein each opening through the first and second tooth spacer body portions is surrounded on all sides by a portion of the tooth spacer body portion containing the opening.

18. The tooth spacer assembly of claim 15 wherein the thickness of the film in the at least partially aligned openings is no greater than 0.0005 inch and the total thickness of first and second tooth spacer body portions together without the film is no greater than 0.004 inch.

19. A tooth spacer for insertion between the interproximal surfaces of at least one pair of adjacent teeth during a dental procedure, the adjacent teeth having a proximate area where the teeth are closest to or in contact with one another, the tooth spacer comprising:
  a first tooth spacer body portion having a first thickness, the first tooth spacer body portion defining at least one first body portion opening for positioning between the interproximal surfaces of adjacent teeth when the tooth spacer is between the teeth;
  a second tooth spacer body portion, the second tooth spacer body portion having a second thickness and defining at least one second body portion opening positioned at least partially in alignment with the at least one first body portion opening;
  at least one layer of film disposed at least partially between the first and second tooth spacer body portions and spanning the aligned portion of the at least one first body portion opening and at least one second body portion opening, the film having a third thickness that is less than the first and second thicknesses; and
  wherein the film and first and second tooth spacer body portions are interconnected.

20. The tooth spacer of claim 19 wherein the first tooth spacer body portion comprises at least two spaced apart first body portion openings and the second tooth spacer body portion comprises at least two second body portion openings, the at least two second body portion openings being in substantial alignment with the at least two first body portion openings, the film spanning the respective aligned at least two first body portion openings and at least two second body portion openings.

21. The tooth spacer of claim 20 wherein each of the first and second body portion openings is entirely surrounded by a portion of the tooth spacer body portion containing the opening.

22. A tooth spacer according to claim 19 wherein the first and second tooth spacer body portions and film are heat fused together.

23. The tooth spacer of claim 19 wherein first and second thicknesses are the same and are each no greater than 0.002 inch and wherein the third thickness is no greater than 0.0005 inch.

24. The tooth spacer of claim 19 wherein the third thickness is from about 0.0003 to 0.0004 inch and the total of the first and second thicknesses is no greater than about 0.003 inch.

25. The tooth spacer of claim 19 wherein the first tooth spacer body portion has a first gingival edge portion and the second tooth spacer body portion includes a second gingival edge portion, at least one of the first and second gingival edge portions including at least one section of a reduced thickness.

26. The tooth spacer of claim 19 including a gingival edge portion when interconnected, the wherein each of the first and second gingival edge portion including at least a section of a reduced thickness.

27. The tooth spacer of claim 26 wherein the at least one section of a reduced thickness is positioned at least partially below the respective at least one first body portion opening and at least one second body portion opening.

28. The tooth spacer of claim 26 wherein the at least a section of a reduced thickness is positioned at a location which is not beneath the at least one first body portion opening and at least one second body portion opening.

29. A tooth spacer for insertion between the interproximal surfaces of at least one pair of adjacent teeth during a dental procedure, the adjacent teeth having a proximate area where the teeth are closest to or in contact with one another, the tooth spacer comprising:
  a first tooth spacer body portion having a first thickness, the first tooth spacer body portion defining at least one first body portion opening for positioning between the interproximal surfaces of adjacent teeth when the tooth spacer is between the teeth;
  a second tooth spacer body portion, the second tooth spacer body portion having a second thickness, the second tooth spacer body portion defining at least one second body portion opening for positioning between the interproximal surfaces of adjacent teeth when the tooth spacer is between the teeth;
  the first and second tooth spacer body portions being positioned such that the at least one first and second body portion openings are substantially in alignment;
  a layer of film disposed at least partially between the first and second tooth spacer body portions and entirely spanning the aligned first and second body portion openings, the film having a third thickness that is less than the first thickness and less than the second thickness, and wherein the thickness of the film is no greater than 0.0005 inch.

30. A tooth spacer according to claim 29 having a gingival edge portion with at least a section thereof having a reduced thickness.

31. A tooth spacer according to claim 30 wherein the first and second tooth spacer body portions together have a total thickness which is no greater than 0.003 inch and wherein the at least one gingival edge section of reduced thickness has a thickness which is no greater than 0.0008 inch.

32. A tooth spacer according to claim 29 wherein the first and second tooth spacer body portions are elongated and each have at least two spaced apart openings which are substantially aligned and spanned by the film.

33. A tooth spacer according to claim 29 wherein the first and second tooth spacer body portions each individually have a thickness which is no greater than 0.002 inch.

34. A tooth spacer according to claim 29 wherein each of the first and second tooth spacer body portions are formed from sheet material which is of a homogenous single layer of material.

35. A tooth spacer according to claim 29 in which the first and second tooth spacer body portions are of metal and the film is optically transparent.

36. A tooth spacer according to claim 29 wherein the first and second tooth spacer body portions and film are heat fused together.

37. A tooth spacer according to claim 36 in which the first and second tooth spacer body portions and the film are heat fused together at spaced apart locations.

38. A tooth spacer according to claim 37 in which the tooth spacer includes only one first tooth spacer body portion, only one second tooth spacer body portion and only one layer of film.

39. A tooth spacer according to claim 37 wherein each first tooth spacer body portion comprises at least two spaced apart first openings and each second tooth spacer body portion comprises at least two spaced apart second openings, the at least two first openings of the first tooth spacer body portion each respectively being substantially aligned with the a respective one of at least two second openings of the second tooth spacer body portions, whereby when the tooth spacer is around a tooth, a first set of aligned first and second openings may be positioned in the proximate area between the tooth and a first adjacent tooth and a second set of aligned first and second openings may be positioned in the proximate area between the tooth and a second adjacent tooth, the second adjacent tooth being on the opposite side of the tooth from the first adjacent tooth.

40. A tooth spacer according to claim 40 in which each of the first and second sets of openings is entirely surrounded by a portion of the respective tooth spacer body portions having the openings.

\* \* \* \* \*